United States Patent
Weithmann

(10) Patent No.: US 6,737,246 B2
(45) Date of Patent: May 18, 2004

(54) METHOD FOR DETECTING PROTEIN INHIBITORS AND LIGANDS OF MEDICAL VALUE

(75) Inventor: Klaus-Ulrich Weithmann, Hofheim (DE)

(73) Assignee: Aventis Pharma Deutschland, GmbH, Frankfurt am Main (DE)

( * ) Notice: Subject to any disclaimer, the term of this patent is extended or adjusted under 35 U.S.C. 154(b) by 0 days.

(21) Appl. No.: 09/876,091

(22) Filed: Jun. 8, 2001

(65) Prior Publication Data

US 2002/0045203 A1 Apr. 18, 2002

(30) Foreign Application Priority Data

Jun. 9, 2000 (DE) ......................................... 100 28 204

(51) Int. Cl.$^7$ ................................................. C12Q 1/34
(52) U.S. Cl. .............................. 435/18; 435/4; 435/69.2
(58) Field of Search ............................. 435/18, 4, 69.2, 435/183

(56) References Cited

U.S. PATENT DOCUMENTS 5,434,052 A * 7/1995 Khanna ....................... 435/7.6
5,770,691 A * 6/1998 Fields et al. ................. 530/328

FOREIGN PATENT DOCUMENTS

| WO | WO 88/09347 | 12/1988 |
| WO | WO 90/12580 | 11/1990 |

OTHER PUBLICATIONS

Stack M. Comparison of Vertebrate Collagenase and Gelatinase Using a New Fluorogenic Substrate Peptide. J of Biological Chemistry 264(8)4277–81, 1989.*
Weithmann K. Effects of Tiaprofenic Acid on Urinary Pyrdinium Crosslinks in Adjuvant Arthritic Rats. Inflamm Res 46(1997)246–252.*
Kolkenbrock H. Biochemical Characterization of the Catalytic Domain of Membrane Type 4 Metalloproteinase. Biol Chem 380(9)1103–1108, Sep. 1999.*
Lazareno, Sebastian, et al., "Allosteric Interactions of Staurosporine and Other Indolocarbazoles with N–[methyl–$^3$H] Scopolamine and Acetylcholine at Muscarinic Receptor Subtypes: Identification of a Second Allosteric Site," Molecular Pharmacology 58:194–207 (2000).
Stack, M. Sharon, et al., "Comparison of Vertebrate Collagenase and Gelatinase Using a New Fluorogenic Substrate Peptide," Journal of Biological Chemistry 264(8):4277–4281 (1989).
Derwent Abstract for WO 88/09347, EP 302,043, and U.S. 5,039,529, Derwent WPI Database.
Bickett, D. Mark et al., A High Throughput Fluorogenic Substrate for Interstitial Collagenase (MMP–1) and Gelatinase (MMP–9), Analytical Biochemistry, 212:58–64 (1993).
Fosang, Amanda J. et al., Aggrecan Is Degraded by Matrix Metalloproteinases in Human Arthritis, J. Clin. Invest., 98(10):2292–2299 (1996).
Knäuper, Vera et al., Biochemical Characterization of Human Collagenase–3, The Journal of Biological Chemistry, 271(3):1544–1550 (Jan. 19, 1996).
Knight, C. Graham et al., A novel coumarin–labelled peptide for sensitive continuous assays of the matrix metalloproteinases, Federation of European Biochemical Societies Letters, 296(3):263–266 (1992).
Massova, Irina et al., Matrix metalloproteinases: structures, evolution, and diversification, The FASEB Journal, 12:1075–1095 (1998).
Nagase, Hideaki et al., Design and Characterization of a Fluorogenic Substrate Selectively Hydrolyzed by Stromelysin 1 (Matrix Metalloproteinase–3), The Journal of Biological Chemistry, 269(33):20952–20957 (1994).
Niedzwiecki, Lisa et al., Substrate Specificity of the Human Matrix Metalloproteinase Stromelysin and the Development of Continuous Fluorometric Assays, Biochemistry, 31:12618–12623 (1992).
Weithmann, K. U. et al., Effects of tiaprofenic acid on urinary pyridinium crosslinks in adjuvant arthritic rats: Comparison with doxycycline, Inflamm. res., 46:246–252 (1997).

* cited by examiner

*Primary Examiner*—Ralph Gitomer
(74) *Attorney, Agent, or Firm*—Finnegan, Henderson, Farabow, Garrett & Dunner, L.L.P.

(57) ABSTRACT

The invention relates to a method for detecting inhibitors or ligands of binding domains, which comprises using a protein which contains at least one catalytic domain and at least one binding domain, incubating said protein with a marker substrate which binds to the catalytic domain of the protein and is converted, with a substrate which can reversibly bind to the catalytic domain and to the binding domain, and with the inhibitor and determining whether the marker substrate is converted by the protein.

2 Claims, No Drawings

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Leu Gly Glu
  1

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Beta-cyclohexyl-Ala
<220> FEATURE:
<221> NAME/KEY: MOD_RES
<222> LOCATION: (4)
<223> OTHER INFORMATION: Cys(Me)

<400> SEQUENCE: 2

Pro Ala Gly Cys His Ala Lys
  1               5
```

```
<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Cyclohexyl-L-alanine
<220> FEATURE:
<221> NAME/KEY: MOD_RES
<222> LOCATION: (4)
<223> OTHER INFORMATION: Nva

<400> SEQUENCE: 3

Pro Xaa Gly Xaa His Ala
 1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Nva

<400> SEQUENCE: 4

Arg Pro Lys Pro Val Glu Xaa Trp Arg Lys
 1               5                  10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Nva

<400> SEQUENCE: 5

Arg Pro Lys Pro Leu Ala Xaa Trp
 1               5
```

METHOD FOR DETECTING PROTEIN INHIBITORS AND LIGANDS OF MEDICAL VALUE

This application claims priority to German 100 28 204.0 filed Jun. 9, 2000.

The present invention relates to a method for detecting substances of medical value, which act in a novel and advantageous manner and which are protein inhibitors.

Enzymes are high molecular weight proteins present in all cells. Enzymes are biocatalysts that make the numerous biochemical metabolic pathways of life possible. Each enzyme is specific for a very particular reaction. Enzymes interact with substrates, wherein the intermediate formed is an enzyme/substrate complex. Following chemical conversion, the converted substrate formed is released into the medium.

Simple enzymes carry only one binding site to take up the substrate. More complex systems comprise a plurality of covalently or noncovalently linked enzyme domains with binding sites A, B, C, D, etc., which are frequently assigned to one enzyme domain each. Said binding sites in turn recognize in the substrate one or more structural or chemically functional groups Z which may be identical (Z1, Z2, Z3, etc.) or different, i.e. Y, X, W, etc.

The corresponding more complex enzyme reactions are composed of a plurality of partial reactions. Thus, domain A can interact with substrate group Z1. Domain B can likewise react with Z1 or with Z2 or with one or more sites Y, X, etc.

A catalytic domain of a protein or enzyme is an amino acid sequence which binds and chemically converts a substrate. A binding domain of a protein or enzyme is an amino acid sequence which binds a substrate reversibly. In these enzymatic systems, it is also possible for binding sites to recognize and bind one or more ligands instead of the substrate; however, said ligands neither behave like a substrate, i.e. they are not chemically converted, nor do they always behave like inhibitors.

When searching for inhibitors or ligands of complex proteins, usually inhibitors of the catalytic domain are found, because said inhibitors lead to a reduction in the chemical conversion of the substrate. Absent or reduced conversions of the marker substrate can also indicate the presence of said inhibitors. It is substantially more difficult to find inhibitors for the binding domain.

It is therefore the object of the present invention to find substances which reduce or essentially prevent binding of substrates to the binding domain of a protein. Said substance may act as inhibitor or may be a ligand.

The object is achieved by incubating a protein, the marker substrate and the substrate with a substance and by determining whether the marker substrate is converted by the protein.

The invention therefore relates to a method to determine whether a test substance is an inhibitor or a ligand of a protein, which method comprises a) using a protein which contains at least one catalytic domain and at least one binding domain, b) using at least one marker substrate which binds to the catalytic domain and is converted, c) using at least one substrate which can bind to the catalytic domain and to the binding domain, d) incubating said protein, the marker substrate and the substrate with the substance or ligand, and e) determining whether the marker substrate is converted by the protein.

Suitable probes are, for example, enzymes which contain at least one catalytic domain and at least one binding domain. The enzymes may, however, also contain 1 to 8 catalytic domains and 1 to 8 binding domains, with the most common enzymes containing 1, 2, 3 or 4 catalytic domains or binding domains. The substrate is a compound which can bind both to the binding domain and to the catalytic domain and which is chemically converted by the catalytic domain but not chemically modified by the binding domain. The marker substrate is a compound which is chemically different from the substrate, is chemically converted by the catalytic domain and allows monitoring of the conversion reaction.

If a test substance binds essentially reversibly or irreversibly to the binding domain of the protein, it may be regarded as an inhibitor of the binding domain of the protein. Not to be limited by theory, inhibition of the binding domain of the protein decreases competition for the catalytic domain of the protein between the marker substrate and the substrate-favoring conversion of the marker substrate-because the substrate generally binds to the binding domain before it is transformed in the catalytic domain of the protein. A desired inhibitor or ligand, would not significantly prevent chemical conversion of the marker substrate by the catalytic domain of the protein because the marker substrate does not need to bind to the binding domain of the protein to be converted. In summary, when an inhibitor or ligand is present, conversion of the substrate by the protein decreases but no inhibition of marker substrate occurs. Conversely, when the test substance is not an effective inhibitor or ligand, there is competition between the marker substrate and the substrate for the catalytic domain of the protein with the end result that conversion of the marker substrate is reduced.

An example of a suitable protein is the enzyme collagenase which comprises at least two covalently linked enzyme domains, one which binds collagen and another which has proteolytic capabilities and cuts the collagen strand. This catalytic proteolytic domain, whether part of the full-length enzyme, i.e. the naturally occurring active enzyme, or just a proteolytic domain prepared by recombination, has the ability to cleave marker substrates of different types.

Examples of suitable marker substrates for collagenase are peptides provided with fluorescent markers or UV markers. Examples of marker substrates for enzymes of this kind are (7-methoxycoumarin-4-yl)acetyl-Pro-Leu-Gly-Leu-(3-[2,4-dinitrophenyl]-L-2,3-diaminopropionyl)-Ala-Arg-NH$_2$ (SEQ ID NO: 1), (C. G. Knight et al, FEBS Letters 296:263–266 (1992)), Dnp-Pro-β-cyclohexyl-Ala-Gly-Cys(Me)-His-Ala-Lys(N-Me-Abz)-Nh$_2$ (SEQ ID NO: 2) (D. M. Bickett et al., Analytical Biochemistry 212:58–64(1993)); Mca-Pro-Cha-Gly-Nva-His-Ala-Dpa-NH$_2$ (SEQ ID NO: 3) (V. Knäuper et al., JBC 271/3, 1544–1550 (1996)); Mca-Arg-Pro-Lys-Pro-Val-Glu-Nva-Trp-Arg-Lys-Dnp-NH$_2$ (SEQ ID NO: 4) (H. Nagase et al., JBC 269/33, 20952–20957 (1994)); Dnp-Arg-Pro-Lys-Pro-Leu-Ala-Nva-Trp-NH$_2$ (SEQ ID NO: 5) (L. Niedzwiecki et al., Biochemistry 31 :12618–12623 (1992)) (D. M. Bickett et al., Analytical Biochemistry 212:58–64 (1993); C. G. Knight, et al, FEBS Letters 296:263–266 (1992); V. Knäuper et al., JBC 271/3, 1544–1550 (1996); H. Nagase et al., JBC 269/33, 20952–20957 (1994); L. Niedzwiecki et al., Biochemistry 31:12618–12623 (1992)), or radiolabeled peptides.

Detection of marker substrates is not limited to fluorescence, UV/Vis, or radioactivity measurements but includes any suitable method known in the art for this purpose, such as HPLC, GC among others.

A suitable substrate for collagenase is collagen. Collagen is a proline-rich structural protein (scleroprotein) and the major component of mesenchymal intercellular supportive substances, which protects against enzymatic attacks. Three protein chains with left-handed helical structure are twisted into a right-handed triple helix (superhelix). 18 collagen types (collagen type I to type XVIII) have been identified, which can be classified according to structure or function into fibrillar, fibril-associated and nonfibrillar collagens.

A particularly suitable substrate for collagenase is type II collagen. This collagen supports the cartilage matrix in joints. In certain diseases such as osteoarthritis and rheumatism the joints are destroyed, in particular due to proteolytic degradation of collagen by collagenases. Inhibitors of enzymes of this kind are known but have the disadvantage of attacking the catalytic domain of the enzyme (K. U. Weithmann et al., Inflamm. Res. 46:246–252 (1997)). Said catalytic domain is part, in a similar structure, of many enzymes and, as a result, the inhibitors act in an unwanted manner upon many enzymes, including those having a vital function (I. Massova et al., The FASEB Journal 12:1075–1095 (1998)). It is the object of the present invention to make better inhibitors, which have a higher specificity for the particular enzymes, available for medicine.

When a marker substrate and type II collagen were incubated with the enzyme collagenase and the marker substrate conversion was determined, it was surprisingly found that the marker substrate conversion was strongly inhibited. This inhibition could be overcome only by large amounts of marker substrate. However, said inhibition of marker substrate conversion did not occur on incubation of only the catalytic domain of collagenase with collagen II and marker substrate.

Surprisingly, it is possible in the method of the invention to identify substances which essentially abolish the inhibition of marker substrate conversion on incubation of complete collagenase with a marker substrate, type II collagen and the test substance. This effect does not appear when only the catalytic domain of collagenase is used instead of complete collagenase.

In contrast, previously reported enzyme inhibitors (K. U. Weithmann et al., Inflamm. Res. 46:246–252 (1997)) cause increased inhibition of marker substrate conversion catalyzed both by the complete enzyme and by the catalytic domain.

Examples of a "protein which contains at least one binding domain and at least one catalytic domain" are the members of the matrixins, the enzymes gelatinase, collagenase-1, neutrophil collagenase or matrix metalloproteinase of type 13 (I. Massova et al., The FASEB Journal 12, 1075–1095 (1998)).

The detection of a test substance is indicated in the method of the invention by the protein converting the marker substrate at a higher conversion rate. In contrast to inhibitors according to the prior art, the substances of the invention do not inhibit the catalytic domain but rather interfere with binding of the substrate to the binding domain (s) of the enzyme. The substances of the invention produce an inhibition with improved specificity, since they do not attack the catalytic domain, which occurs in many enzyme types.

In one example of the method of the invention, the protein used is collagenase, the substrate used is type II collagen and the marker substrate used is (7-methoxycoumarin-4-yl) acetyl-Pro-Leu-Gly-Leu-(3-[2,4-dinitrophenyl]-L-2,3-diaminopropionyl)-Ala-Arg-NH$_2$ (SEQ ID NO: 1).

The invention further relates to a test kit for carrying out the method of the invention, which comprises the components A) a protein which has at least one catalytic domain and at least one binding domain,
B) a marker substrate which binds to the catalytic domain and is converted, and
C) a substrate which can bind to the catalytic domain and to the binding domain.

The efforts to find effective compounds for the treatment of connective tissue disorders have resulted in the finding that the substance 4-(diphenylmethylene)-1-[4-(p-fluorophenyl)-4-phenyl-3-butenyl]piperidine, detected by the method of the invention, is a strong inhibitor of metalloproteinases. In this connection, particular importance is attached to the inhibition of stromelysin (matrix metalloproteinase 3), neutrophil collagenase (MMP-8) and aggrecanase, since these enzymes play a substantial part in the degradation of proteoglycans as important components of cartilage tissue (A. J. Fosang et al. J. Clin. Invest. 98:2292–2299 (1996)).

The invention also relates to pharmaceuticals which comprise an active content of 4-(diphenylmethylene)-1-[4-(p-fluorophenyl)-4-phenyl-3-butenyl]piperidine and/or of a physiologically tolerated salt of 4-(diphenylmethylene)-1-[4-(p-fluorophenyl)-4-phenyl-3-butenyl]piperidine and/or of a stereoisomeric form of 4-(diphenyl-methylene)-1-[4-(p-fluorophenyl)-4-phenyl-3-butenyl]piperidine together with a pharmaceutically suitable and physiologically tolerated carrier, additive and/or other active ingredients and excipients.

In addition to the compound 4-(diphenylmethylene)-1-[4-(p-fluorophenyl)-4-phenyl-3-butenyl]piperidine, owing to the pharmacological properties, protamine sulfate and also oligosaccharides and tetrasaccharides, which are obtained from heparin degradation, are also suitable for the prophylaxis and therapy of all those disorders whose course involves increased activity of matrix-degrading enzymes such as collagenases, metalloproteinases or aggrecanase. This includes degenerative joint disorders such as osteoarthroses, spondyloses, chondrolysis after joint trauma or prolonged immobilization of joints after meniscus or patella injuries or tearing of ligaments. This further includes also disorders of the connective tissue such as collagenoses, periodontal disorders, wound-healing disturbances and chronic disorders of the locomotor apparatus such as inflammatory, immunologically or metabolically caused acute and chronic arthritis, arthropathies, myalgias and disorders of bone metabolism. Furthermore, 4-(diphenylmethylene)-1-[4-(p-fluorophenyl)-4-phenyl-3-butenyl]piperidine is suitable for the treatment of ulceration, atherosclerosis and stenoses. In addition, 4-(diphenylmethylene)-1-[4-(p-fluorophenyl)-4-phenyl-3-butenyl]piperidine is suitable for the treatment of inflammations, cancers, formation of tumor metastases, cachexia, anorexia and septic shock. The pharmaceutical of the invention is generally administered orally or parenterally. Rectal or transdermal administration is also possible.

The invention also relates to a method for preparing a pharmaceutical, which comprises bringing 4-(diphenylmethylene)-1-[4-(p-fluorophenyl)-4-phenyl-3-butenyl]piperidine together with a pharmaceutically suitable and physiologically tolerated carrier and, where appropriate, further suitable active ingredients, additives or excipients into a suitable administration form.

Examples of suitable solid or liquid pharmaceutical preparation forms are granules, powders, coated tablets, tablets, (micro)capsules, suppositories, syrups, elixirs, suspensions, emulsions, drops or injectable solutions and also products with protracted release of active ingredient, whose preparation makes use of common auxiliaries such as carriers, disintegrants, binders, coating agents, swelling agents, glidants or lubricants, flavorings, sweeteners and solubilizers. Frequently used excipients which may be mentioned are magnesium carbonate, titanium dioxide, lactose, mannitol and other sugars, talc, lactoprotein, gelatin, starch, cellulose and its derivatives, animal and vegetable oils such as cod liver oil, sunflower, peanut or sesame oil, polyethylene glycol and solvents such as, for example, sterile water and mono- or polyhydric alcohols such as glycerol.

The pharmaceutical products are typically prepared and administered in dosage units, each unit containing as active constituent a particular dose of the compound of the invention, 4-(diphenylmethylene)-1-[4-(p-fluorophenyl)-4-phenyl-3-butenyl]piperidine. In the case of solid dosage units such as tablets, capsules, coated tablets or suppositories, said dose can be up to about 1000 mg, but is typically from about 50 to about 300 mg, and in the case of injection solutions in ampoule form up to about 300 mg, but typically from about 10 to about 100 mg. For the treatment of an adult patient about 70 kg in weight, daily doses of about 20 mg to about 1000 mg, typically from about 100 mg to about 500 mg, of active ingredient are indicated. Under certain circumstances, however, higher or lower daily doses may also be appropriate. The daily dose can be administered either by single administration in the form of an individual dosage unit or else of several smaller dosage units or by multiple administration of divided doses at particular intervals.

The invention further relates to an inhibitor which is obtainable through detection by the method of the invention.

EXAMPLES
Preparation of the COMPONENTS
COMPONENT A)
Enzyme Solution

MMP-13 was obtained as a commercial product (Cat. No. HM 13110010) from Invitek GmbH, Berlin, Germany, activated according to the manufacturer's instruction, and diluted to 10 $\mu$g/10 ml with TCB buffer. TCB buffer was prepared by dissolving 10 mM tris(hydroxymethyl)aminomethane (Sigma-Aldrich Chemie GmbH, Deisenhofen, Germany) in water and adjusting the pH to 7.5 with HCl. 100 mM $CaCl_2 \times 2H_2O$ (Merck KGaA, Darmstadt, Germany) and 0.05% of Brij 35 solution, 30% (w/v) (Sigma-Aldrich Chemie GmbH, Deisenhofen, Deutschland), are added to said solution.
COMPONENT B)
Marker Substrate Solution A solution of 10 mmol/l (7-methoxycoumarin-4-yl)acetyl-Pro-Leu-Gly-Leu-(3-[2,4-dinitrophenyl]-L-2,3-diaminopropionyl)-Ala-Arg-$NH_3$ (SEQ ID NO: 1). (Bachem Biochemica GmbH, Heidelberg, Germany) in dimethyl sulfoxide (DMSO) (Riedel-de Haen AG, Seelze, Germany) was diluted 1:40 (v/v) with water.

COMPONENT C)
Collagen II Solution 10 mg of human collagen 11 (Biocon, Potsdam, Germany) were dissolved in 2400 $\mu$l of 10 mmol/l acetic acid (72 hours at 4° C.), and then 1300 $\mu$l of a sodium bicarbonate solution (250 mmol/l) $CaCl_2 \times 2H_2O$ (Merck KGaA, Darmstadt, Germany) were added dropwise.
COMPONENT D)

Test substance (suspected inhibitor or ligand), typically dissolved in water at an appropriate concentration relative to the amount of enzyme used.
Test Protocol The components A) (25 $\mu$l), B) (5 $\mu$l), C) (10 $\mu$l) and D) (10 $\mu$l) were mixed in a total volume of 50 $\mu$l, and fluorescence was measured in a commercial spectrofluorimeter after 15 minutes (excitation at 330 nm, emission at 390 nm, Spectrafluor plus, Tecan Deutschland GmbH, Crailsheim, Germany).

Enzyme and inhibitor were preincubated at room temperature for 15 min. The reaction was started by adding 5 $\mu$l of marker substrate solution (component B at 25 $\mu$M).

The fluorescence in example 1 was set at 100%, and the measured values of the other examples are based on this value. Table 1 shows the results.

TABLE 1

|  | Example 1 | Example 2 | Example 3 | Example 4 | Example 5 | Example 6 |
|---|---|---|---|---|---|---|
| Component A | yes | yes | Yes | yes | yes | yes |
| Component B | yes | yes | Yes | yes | yes | yes |
| Component C | no | yes | Yes | yes | yes | yes |
| Component D | no | no | 200 $\mu$mol/l substance (I) | 200 $\mu$mol/l doxycycline | 50 $\mu$g/well tetra-saccharide | 60 $\mu$g/well protamine sulfate |
| Measured value | 100% | 49% | 59% | 0% | 72% | 73% |

Examples 3, 5 and 6 illustrate the method of the invention, which makes it possible to detect novel inhibitors or ligands. These are distiguished by producing fluorescence values of 50–99% at a concentration of up to 500 $\mu$mol/l, typically 50 $\mu$mol/l or less, in particular also starting from 1 nmol/l, and in exceptional cases down to 0.1 nmol/l.

Example 1

In general, inhibitor or ligands of the invention can be detected by comparing the transformation of the marker substrate in the presence of the test substance with the corresponding transformation occurring in appropriate control mixtures. One such control mixture contained the enzyme and the substrate marker but no substrate or test substance (e.g., Example 1 in Table 1). The transformation of the marker substrate in this control mixture indicated the maximum conversion possible for the marker substrate because there was no inhibition of the catalytic domain.

Example 2

Another control mixture contained the enzyme the substrate marker and the substrate but no test substance (e.g., Example 2 in Table 1). Transformation of the marker substrate in this second control mixture reflected competitive inhibition of the catalytic domain by both the substrate and the marker substrate.

If conversion of the marker substrate in the presence of a test substance is between the values obtained with these two control mixtures, an inhibitor or ligand of the invention has been found.

Conversely, if transformation of the marker substrate is lower than the value obtained with the second control mixture, then the test substance is likely competing with both the substrate and the marker substrate for binding to the catalytic site.

In general, transformation of the marker substrate can be detected by a variety of methods known in the art that include, but are not limited to, the determination of the rate of transformation of the marker substrate at a given moment or the determination of the overall conversion of the marker substrate after incubation for a suitable period of time.

Example 3

200 µmol/l of the substance of the invention, 4-(diphenylmethylene)-1-[4-(p-fluorophenyl)-4-phenyl-3-butenyl]piperidine, (I)

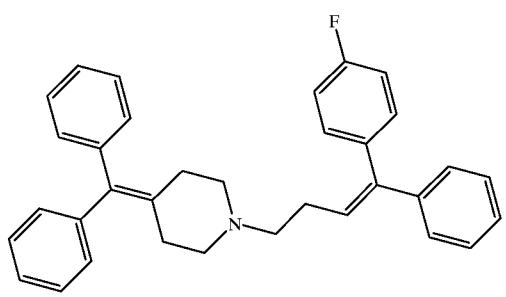

(I)

produced a value of 59%.

Example 4

Those substances producing measured values of 49% or less, decreasing down to zero, have to be distinguished from the substances of the invention. For example, 200 µmol/l doxycycline (K. U. Weithmann et al., Inflamm. Res. 46:246–252 (1997)) produced a value of 0.

Example 5

50 µg/50 µl tetrasaccharide GT8021 (Neoparin, Inc., 14274 Wicks Blvd, San Leandro, Calif. 94577). According to the invention, 50 µg/50 µl tetrasaccharide produced a value of 72%.

Example 6

60 µg/50 µl protamine sulfate P-4020 (Sigma-Aldrich Chemie GmbH, Deisenhofen, Germany). According to the invention, 60 µg/50 µl protamine sulfate produced a value of 73%.

I claim:

1. A method to determine whether a test substance inhibits or acts as a ligand of at least one binding domain of a protein, comprising:
   incubating said test substance with a mixture,
   wherein said mixture comprises:
   a) the protein,
   b) at least one marker substrate, and
   c) at least one substrate; and
   determining whether the test substance inhibits or acts as a ligand of at least one binding domain of the protein by comparing the conversion of the marker substrate in the presence of the test substance with the corresponding conversion in control mixtures A and B,
   wherein the protein contains at least one catalytic domain and at least one binding domain,
   wherein the marker substrate is converted by said at least one catalytic domain of the protein,
   wherein the substrate is capable of binding to said at least one catalytic domain and to said at least one binding domain of the protein,
   wherein the control mixture A comprises the protein and the marker substrate; and the control mixture B comprises the protein, the substrate, and the marker substrate, and
   wherein the test substance is an inhibitor or ligand of said at least one binding domain of the protein if the conversion of the marker substrate in the presence of the test substance is between the values obtained with control mixtures A and B.

2. The method as claimed in claim 1, wherein the protein is collagenase, the substrate is collagen, and the marker substrate is (7-methoxycoumarin-4-yl)acetyl-Pro-Leu-Gly-Leu-(3-[2,4-dinitrophenyl]-L-2,3-diaminopropionyl)-Ala-Arg-NH$_2$ (SEQ ID NO: 1).

* * * * *